Dec. 13, 1960
O. O. DUNHAM
CHRYSANTHEMUM PLANT
Filed July 27, 1959
Plant Pat. 2,005
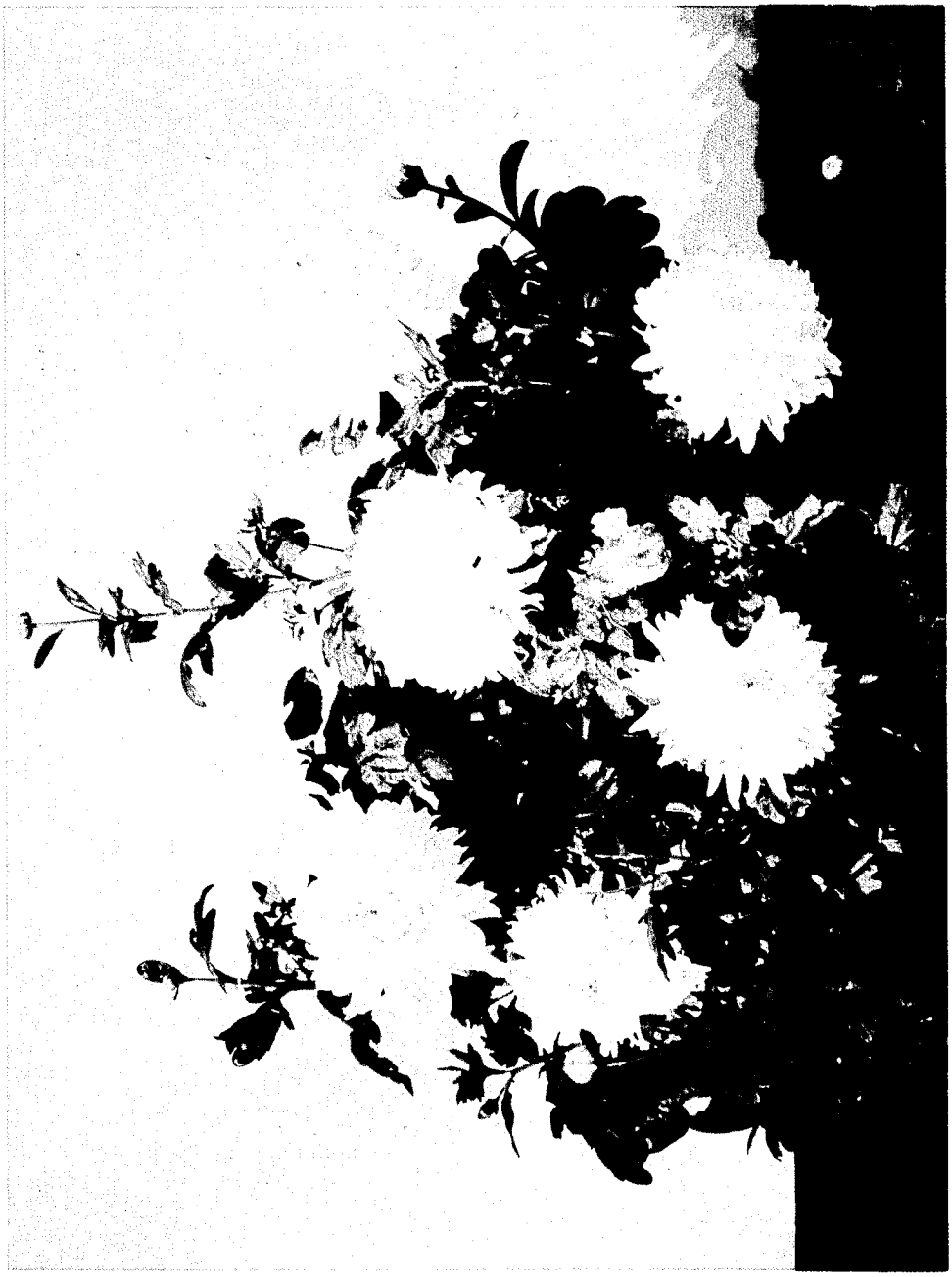
Inventor
O. O. Dunham
by Robb & Robb
attorneys United States Patent Office Plant Pat. 2,005
Patented Dec. 13, 1960

2,005

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,948

1 Claim. (Cl. 47—60)

My present invention comprises a new and distinct variety of chrysanthemum plant, which is the result of crossing the variety "Satin" (unpatented), a plant of my own introduction, with the unpatented variety "Modesty" likewise a plant of my own introduction.

The object of this invention has been to produce a new variety of chrysanthemum of the indicum type having purer white blossoms.

The development of the present new variety has taken place during the course of a program of careful selection and cross-breeding which I have been conducting for a considerable period of time, in an endeavor to produce new varieties of chrysanthemums which will have earlier and hardier characteristics, together with novel different colors of blooms.

The result of the specific hybridization previously mentioned has been to produce my present new and distinct variety of chrysanthemum plant characterized by the lighter than brilliant yellow center and purer white general tonality and the large size and hardiness of its blooms, the very double arrangement of its petals, the early, continuous and long blooming period and its larger and more abundant foliage.

More specifically, the blooms of my new variety are of a purer white color and have been grown in the vicinity of Niles, Michigan, under uniform culture.

Although this new variety resembles both its parents in some respects, it obtains its earliness from the parent "Modesty" and hardiness from the parent "Satin." The resulting variety is earlier and hardier than either of its parents.

To compare the color of the bloom of my new variety with the color of the blooms of "Satin" which is the pollen parent, is to point out that my new variety has a much purer white appearance and in addition has the lighter than brilliant yellow center in the fully blown bloom.

To compare the color of the blooms of my new variety with the seed parent, "Modesty" is also to point out that the new variety is of a much purer white and has the lighter than brilliant yellow center.

While it may also be noted that the seed parent "Modesty" has a slight blush, it is not a characteristic of the new variety hereof.

Under the conditions of culture previously mentioned, in the region of Niles, Michigan, the plants of my new variety have been found to have very substantially improved foliage including larger and more abundant such foliage.

When the plants are grown in the region of Niles, Michigan, blooms begin to appear in mid-September and bloom very profusely and continuously until a killing frost.

The observations upon which the description herein is based, were made in the vicinity of Niles, Michigan, in late September.

It may be pointed out further that the bloom of my new variety are very large, having an average size when fully expanded of 6½ inches (disbudded). The blooms appear in clusters somewhat irregular in nature and on long, strong stems with very double petallage.

The buds of my new variety when petals begin to unfurl appear to be a white shading to a creamy white in the center with the inside of the petals and reverse of the petals a white, both being purer white than the parent varieties "Modesty" and "Satin."

My new variety has been asexually reproduced by cuttings, in the vicinity of Niles, Michigan.

My new variety has been found to retain its distinctive characteristics through successive asexual reproductions.

The accompanying drawing, forming a part hereof, shows a typical plant of my new variety of chrysanthemum.

The following is a detailed description of my new variety of chrysanthemum plant, the color reference being to the Nickerson Color Fan published by Munsell Color Company:

Parentage: Seedling.
- *Seed parent.*—"Modesty" (unpatented).
- *Pollen parent.*—"Satin" (unpatented).

Classification: Botanic—*Chrysanthemum indicum.*

*Flower*

Blooming habit: Blooms early from mid-September to killing frost and profusely and continuously during such time.

Bud:
- *Size.*—Large.
- *Form.*—Short with flat top. Not affected by hot or wet weather. Sepals of no consequence.
- *Color.*—When petals begin to unfurl—white shading to creamy white in the center. When half blown: inside of petals—white; reverse of petals—white.
- *Peduncle.*—Very long.
- *Aspect.*—Rough.
- *Strength.*—Stiff; erect.
- *Opening.*—Bud opens well; somewhat affected by adverse conditions.

Bloom:
- *Size.*—Very large.
- *Average size when fully expanded.*—6½ inches (disbudded).
- *Borne.*—In clusters; irregular.
- *Stems.*—Long; strong.
- *Form.*—Flat. Permanance—retains its form to the end.
- *Petalage.*—Very double. Number of petals under normal conditions—innumerable.
- *Color.*—Center of flower—lighter than 2.5Y 9/9 Munsell Hue 2.5Y. Outer petals—white. Base of petals (singlet)—lighter than 2.5Y 9/9 Munsell Hue 2.5Y. Inside of petals—white. Reverse of petals—white. General tonality from a distance—white.
- *Discoloration.*—First week—retains the same color. Second week—retains much the same color. Third week—retains much the same color.

Petals:
- *Texture.*—Thin. Affected somewhat by bleaching in hot weather. Affected by some fungus infection in wet weather.
- *Appearance.*—Inside—velvety; outside—satiny.
- *Form.*—Pointed.
- *Arrangement.*—Imbricated.
- *Persistence.*—Hang on and dry.
- *Lastingness.*—On the plant—very long. As cut flower—long.

Genital organs:
- *Stamens.*—Small; few. Color—yellow. Arrangement—regular around styles.

*Stamens, filaments.*—Short. Color—white.
*Styles.*—Columnar.
*Stigmas.*—White.
*Ovaries.*—All enclosed in calyx.

Form: Bush.

Growth: Vigorous; dwarf; branching; compact.

Foliage:

*Size.*—Large.
*Quantity.*—Abundant.
*Color.*—New foliage: upper side—normal green; under side—light green. Old foliage: upper side—dark green; under side—dark green.
*Shape.*—Three lobed.
*Texture.*—Upper side—smooth; flat. Under side—velvety. Ribs and veins—ordinary.

*Edge.*—Smooth.
*Leaf stem.*—Green in color.
*Stipules.*—Short.
*Disease resistant.*—Under certain conditions susceptible to mildew.

I claim:

A new and distinct variety of chrysanthemum plant substantially as herein disclosed, characterized as to novelty by the lighter than brilliant yellow center and purer white general tonality, and the large size and hardiness of its blooms, the very double arrangement of its petals, the early, continuous and long blooming period and its larger and more abundant foliage.

No references cited.